(12) United States Patent
Malek et al.

(10) Patent No.: US 10,258,284 B1
(45) Date of Patent: Apr. 16, 2019

(54) IMPLANT IN MIDDLE MENINGIAL-ARTERY

(71) Applicant: Tufts Medical Center, Inc., Boston, MA (US)

(72) Inventors: Adel M. Malek, Weston, MA (US); Carl Heilman, Wayland, MA (US)

(73) Assignee: Tufts Medical center, Inc., Boston, MA (US)

( * ) Notice: Subject to any disclaimer, the term of this patent is extended or adjusted under 35 U.S.C. 154(b) by 0 days.

(21) Appl. No.: 15/946,078

(22) Filed: Apr. 5, 2018

(51) Int. Cl.
| | |
|---|---|
| *A61B 5/02* | (2006.01) |
| *A61B 5/00* | (2006.01) |
| *A61N 1/05* | (2006.01) |
| *A61N 1/365* | (2006.01) |
| *A61N 7/00* | (2006.01) |
| *A61B 5/01* | (2006.01) |
| *A61B 5/145* | (2006.01) |
| *A61B 5/11* | (2006.01) |
| *A61B 5/03* | (2006.01) |
| *A61B 5/1455* | (2006.01) |
| *A61B 5/0478* | (2006.01) |
| *A61N 5/06* | (2006.01) |
| *A61B 5/16* | (2006.01) |

(52) U.S. Cl.
CPC ............ *A61B 5/6882* (2013.01); *A61B 5/002* (2013.01); *A61B 5/0071* (2013.01); *A61B 5/01* (2013.01); *A61B 5/031* (2013.01); *A61B 5/0478* (2013.01); *A61B 5/1126* (2013.01); *A61B 5/14539* (2013.01); *A61B 5/14546* (2013.01); *A61B 5/14553* (2013.01); *A61N 1/0539* (2013.01); *A61N 1/365* (2013.01); *A61N 5/0601* (2013.01); *A61N 7/00* (2013.01); *A61B 5/165* (2013.01); *A61B 5/4094* (2013.01); *A61B 5/746* (2013.01); *A61B 2560/0214* (2013.01); *A61N 2005/0602* (2013.01)

(58) Field of Classification Search
None
See application file for complete search history.

(56) References Cited

U.S. PATENT DOCUMENTS

| | | | |
|---|---|---|---|
| 6,016,449 | A | 1/2000 | Fischell |
| 6,061,593 | A | 5/2000 | Fischell |
| 6,128,538 | A | 10/2000 | Fischell |
| 6,134,474 | A | 10/2000 | Fischell |
| 6,354,299 | B1 | 3/2002 | Fischell |
| 6,360,122 | B1 | 3/2002 | Fischell |
| 6,427,086 | B1 | 7/2002 | Fischell |

(Continued)

OTHER PUBLICATIONS

Shal et al., "Endovascular Treatment of a Traumatic Pseudo Aneurysm of the Middle Meningeal Artery," *Radiology Case Reports*, vol. I-3(73-76) 2006.

*Primary Examiner* — Ankit D Tejani
(74) *Attorney, Agent, or Firm* — Occhiutu & Rohlicek LLP

(57) ABSTRACT

An implant sized and shaped to be endovascularly delivered to the middle meningeal artery includes a carrier that carries a payload between first and second ends thereof. An anchor mechanism associated with the implant transitions into a swollen state in response to exposure to bodily fluids. In the swollen state, said anchor mechanism anchors the implant to the middle meningeal artery. Before or during the transition, the anchor mechanism permits endovascular delivery of the implant to the middle meningeal artery.

30 Claims, 8 Drawing Sheets

(56) References Cited

U.S. PATENT DOCUMENTS

| | | |
|---|---|---|
| 6,459,936 B2 | 10/2002 | Fischell |
| 6,647,296 B2 | 11/2003 | Fischell |
| 7,074,189 B1* | 7/2006 | Montegrande ........... A61B 5/06 |
| | | 600/462 |
| 2001/0051819 A1 | 12/2001 | Fischell |
| 2001/0056290 A1 | 12/2001 | Fischell |
| 2002/0002390 A1 | 1/2002 | Fischell |
| 2002/0099412 A1 | 7/2002 | Fischell |
| 2007/0100410 A1* | 5/2007 | Lamson ................. A61N 1/056 |
| | | 607/119 |
| 2008/0262330 A1 | 10/2008 | Reynolds |
| 2012/0330196 A1* | 12/2012 | Nita ....................... A61N 7/022 |
| | | 601/2 |
| 2013/0172774 A1* | 7/2013 | Crowder ................. A61B 5/04 |
| | | 600/544 |
| 2013/0211489 A1* | 8/2013 | Makower ................ A61F 2/915 |
| | | 623/1.2 |
| 2016/0317328 A1* | 11/2016 | Berez ....................... A61F 2/82 |
| 2017/0071490 A1* | 3/2017 | Parker ................ A61N 1/36125 |
| 2017/0165488 A1* | 6/2017 | Bharmi .............. A61N 1/36139 |
| 2017/0296198 A1* | 10/2017 | Rudakov .......... A61B 17/12109 |
| 2017/0333720 A1* | 11/2017 | Astrom ................ A61N 1/0534 |

* cited by examiner

IMPLANT IN MIDDLE MENINGIAL-ARTERY

FIELD OF INVENTION

This invention relates to surgery, and in particular, to brain surgery.

BACKGROUND

It is sometimes useful to measure physical parameters within the brain. It is also sometimes useful to deliver energy to structures within the brain.

A difficulty arises from the presence of a skull. Although the skull serves useful functions, it hampers the ability to make measurements of activity within the brain and to deliver energy therein.

Of course, it is always possible to make holes in the skull and insert various devices through those holes. However, this is a somewhat invasive procedure that carries certain risks.

It is also possible to place electrodes on the scalp. However, there are quite a few layers between the scalp and the brain. Thus, a signal of interest must pass through many layers before reaching the electrodes. This results in considerable attenuation.

Additionally, stray electrical signals from nerves that actuate muscles in the vicinity of the scalp and large signals from contracting muscle fibers themselves can interfere with the signal of interest.

To make matters worse, the scalp is not completely stationary relative to the skull. Thus, when an electrode is attached to the scalp, it can move relative to the brain. These movements cause artifacts in the measured signal and impede correct accurate registration. All of this combines to result in an often unacceptably low signal-to-noise ratio for measurements and in inaccurate delivery of energy when attempting to effect a stimulus.

In a similar fashion, it would be advantageous to place other types of optical or sonic stimulators/transducers such as those measuring oxygen saturation closer to the brain without having to be limited by traversing the skull, muscle, and scalp overlying the brain.

SUMMARY

The invention is based on the recognition that the middle meningeal-artery has certain properties that make it eminently useful as a privileged location for placement of an implant that will interact with the brain. Such interaction can take the form of measurement or stimulation.

In pursuit of its mission, the implant can carry a variety of sensors, emitters, and transducers for measurement of a variety of physical parameters that are associated with tissues within the skull. An implant as described herein is also useful for placement of diagnostic or therapeutic stimulators. Such stimulators can include electrical, sonic, or photonic stimulators in exceptionally close proximity to the brain surface without requiring penetration of the skull using invasive surgical techniques.

Other examples of stimulators include ultrasonic stimulators, infrasonic stimulators, megasonic stimulators, stimulators that output pressure waves at audible frequencies, and stimulators that output longitudinal pressure waves at frequencies between $10^n$ Hz and $10^{n+1}$ Hz, where n is an integer between 0 and 9.

Additional stimulators include those that output electromagnetic radiation at a variety of frequencies. These include stimulators that output radiation at frequencies between $10^n$ Hz and $10^{n+1}$ Hz, where n is an integer between 0 and 14.

Additional examples of stimulators include those that output a dc voltage or current and those that output an ac voltage current.

Yet other examples of stimulators include stimulators that output radio waves, stimulators that output microwaves, stimulators that output infrared radiation, stimulators that output visible light, stimulators that output ultraviolet light, X-ray stimulators, and gamma-ray stimulators.

Yet other examples of stimulators include stimulators that cause net energy transfer into the human body. These stimulators include those that cause energy transfer via deposition from waves, including mechanical waves, electromagnetic waves, and pressure waves.

Yet other stimulators include those that transfer mechanical energy, those that transfer chemical energy, those that transfer electrical energy, and those that transfer thermal energy.

Also among the stimulators are those that contain radioisotopes that emit nuclear radiation for targeting specific regions of the brain.

In one aspect, the invention features an implant that is sized and shaped to be delivered to the middle meningeal artery by being passed through blood vessels. The implant includes a carrier that carries a payload and an anchor mechanism that anchors the implant to the middle meningeal artery.

In some embodiments, the implant also has an anchor mechanism that transitions into a swollen state. In the swollen state, the anchor mechanism anchors the implant to the middle meningeal artery. Prior to completing its transition into the swollen state, the anchor mechanism permits endovascular delivery of the implant to the middle meningeal artery. Among the foregoing embodiments are those in which the anchor mechanism swells in response to exposure to bodily fluids.

In some embodiments, the implant has a diameter of less than about 1.8 millimeters. In others, the implant has a diameter of less than about 1.5 millimeters.

In some embodiments, the implant is resorbable. Also among the embodiments are those in which the implant is a long-term implant and those in which it is a short-term implant. As used herein, long-term implants are those that can be safely used for more than thirty days. All other implants are short-term implants.

Embodiments include embodiments in which the anchor mechanism comprises first and second anchors disposed at one or more locations on the carrier. Among these are embodiments in which there are anchors at corresponding first and second ends of the carrier, embodiments in which the anchor mechanism comprises a toroidal anchor disposed around the implant, and embodiments in which the anchor mechanism comprises a hydrogel layer that surrounds the implant. In more complex devices, there may be more than two anchors.

Also among the embodiments are those in which the anchor mechanism comprises toroidal anchors that are axially displaced from each other.

Other embodiments include anchors that engage the arterial wall at different circumferential angles. Such anchors include stellar anchors. These embodiments include those in which the anchors engage at points that separated by the same angular extent or at points separated by different angular extents.

Also among the embodiments are those that use strut-type anchors similar to those used in stents. These include open-cell, closed-cell, and braided configurations.

In other embodiments, the anchor mechanism responds to exposure to external inputs by transitioning from a first size that permits delivery of the implant to the middle meningeal artery and a second size that is too large to pass through the middle meningeal artery. Among these embodiments are those in which exposure to bodily fluids causes swelling of the anchor mechanism from the first size to the second size.

In other embodiments, the implant changes mass between the time it enters the body and the time it is implanted. This extra mass can come from a variety of sources. One way that mass changes is from absorbing bodily fluids. Another source of mass is from an infusion of fluid, such as saline, through a small catheter. Yet another source of mass is fluid that is infused once the implant has reached the correct position. This fluid causes anchoring at the desired position to occur. Examples of fluid include saline and a liquid embolic glue, an example of which is ONYX™.

In another embodiment, the implant is contained within a stent outer configuration which is retrievable.

In some embodiments, the anchor mechanism comprises first and second toroidal anchors that flank the carrier.

Other embodiments feature an occlusion of the middle meningeal artery. In these embodiments, the anchor mechanism begins to form the occlusion during delivery of the implant to the middle meningeal artery and completes formation of the occlusion after the implant has been delivered to the middle meningeal artery.

In yet other embodiments, the anchor mechanism comprises an annular anchor that spontaneously transitions from a first state into a second state. In the first state, the annular anchor has an outer diameter that is smaller than an inner diameter of the middle meningeal artery. In the second state, the annular anchor would have an outer diameter larger than an inner diameter of the middle meningeal artery if the annular anchor were outside of the middle meningeal artery.

Embodiments also include those in which the carrier comprises a tubular body and the payload is disposed inside the tubular body. However, the payload can also extend outside any body. For example, in some embodiments, the carrier comprises a flexible wire and the payload is disposed on the flexible wire. Among these are embodiments in which the anchor mechanism includes anchors at either end or both ends of the flexible wire.

In some embodiments, the implant comprises an antenna and communication circuitry for communication with one or more other devices. In some embodiments, this other device is a controller outside a patient into which the implant has been implanted. In other embodiments, these devices are similar implants that are also present in the patient's head. In such embodiments, the various implants form a personal-area network in which the implants communicate with each other. In some of these personal-area networks, the implants communicate without having to communicate with an external controller. Communication between such implants includes data exchange, exchange of control instructions, or a combination of both. In some such networks, one implant takes the role of master while one or more implants take the roles of slaves. In these embodiments, the master transmits control instructions to one or more slaves, which then execute those instructions.

In some embodiments, a first implant sends a signal to a second implant across an expanse of tissue. Based on the properties of the received signal, it is possible to make inferences concerning the nature of the intervening tissue. The signal can be an acoustic signal or an electromagnetic signal. This signaling can be repeated over time without outside intervention to provide a way to track time-varying phenomena, such as swelling of the brain or concentration of water in cerebral matter.

In other embodiments, the implant comprises a power supply for powering a communication system configured to communicate with a controller outside a patient into which the implant has been implanted.

In yet other embodiments, the implant comprises passive circuitry configured to communicate in response to receiving power from outside a patient into which the implant has been implanted.

Also among the embodiments are those that include a power source. In some embodiments, the power source is a battery. Of particular usefulness is a battery that can be recharged inductively from an external wireless charger. In other embodiments, the power source is one that harvests mechanical energy and stores it for future release. Such mechanical energy can be derived from a patient's own movement. A particularly rich source of mechanical energy is the patient's gait. Other sources of energy exist. These include the patient's arterial pulsations and the variation and pulsatile nature of the patient's intracranial pressure.

A variety of payloads is possible either singly in combination. For example, in some embodiments, the payload comprises an electrical transducer. In others, the carrier is a flexible carrier and the payload comprises a plurality of nodes disposed on the flexible wire. These nodes can be implemented as electrodes that can then be used either for receiving signals or for brain stimulation.

In some embodiments, the payload comprises a communication system that receives a signal from a collateral implant and uses the signal as a basis for feedback control the collateral implant. Among these are embodiments that provide feedback control of a pacemaker. Also among these are embodiments in which a first implant is close to a sensory cortex and a second implant is close to a motor cortex. In such embodiments, first implant could send instructions to the second implant in response to receiving sensory information from the sensory cortex.

Other examples of payloads include an electrode, a glucose sensor, a neurotransmitter sensor, an accelerometer, a gyrometer, a chemical sensor, an NIR laser and receiver for use in pulse oximetry, a light source for use in optogenetic stimulation, a source of acoustic energy, a sensor for receiving acoustic energy, a biomarker chip, a temperature sensor, an instrument for measuring hydrogen ion concentration, an ultrasound transducer, an infrared transducer, a fluorescence detector, a motion sensing apparatus, and a pressure sensor.

Some embodiments feature a payload that comprises a membrane configured to contact a wall of the artery that faces dura matter and a pressure sensor in contact with the wall for measuring intra-cranial pressure.

Further embodiments include those in which the carrier comprises a flexible wire and the payload comprises nodes along the wire, each of the nodes being selected from the group consisting of a sensor and a stimulator. In some of these embodiments, an anchoring system comprises a stent that engages the wire. In others, plural stents engage the wire at different locations, for example at the ends of the wire.

The invention thus provides ways to measure electrical activity occurring in tissues within the skull. This is a useful way to evaluate brain function, including the detection of a seizure, or to moderate other implanted devices or pharmacological agent infusions or treatments.

The implant provides ways to measure pressure, and in particular, intracranial pressure. Elevated intracranial pressure interferes with brain perfusion and can thus result in a variety of significant ailments. Among the more undesirable ailments is brain death.

The implant also provides a way to measure brain-tissue perfusion. Such measurements are useful for early detection of against insufficient blood flow that often results from traumatic brain injury or from a vasospasm that arises from rupture of a brain aneurysm. Early detection of a decrease in brain-tissue perfusion provides time to carry out corrective measures, thus reducing the risk of brain ischemia and irreversible stroke.

The implant also provides a way of following up on adjacent brain tumor recurrence or regrowth after resection. This could be achieved by systemic administration of the fluorescent marker that avidly binds to tumor tissue which the implant can measure thanks to its light emitting and receiving properties. Tumor progression can also be monitored by measuring nearby tissue properties using either near-infrared or sonic transduction to measure local changes in tissue properties after removal of the brain tumor. Furthermore, the implant could modulate local drug delivery adjacent to its implant site by transmitting either light or sound frequency to aid in the local release or activation of systemically delivered pharmaceuticals.

The implant benefits from a location that is relatively fixed and secure. When deployed, the implant lies within a vascular channel that is also nestled within a groove in a bone. This is an unusual circumstance. Most blood vessels are surrounded by relatively soft tissue such that the blood vessel can shift its position in response to applied forces. This means that if an implant is placed within such a blood vessel, one cannot be truly sure of its position relative to anything in particular, particularly during acceleration and deceleration such as traumatic injury.

Because it is cradled within a bony groove, the middle meningeal artery does not shift easily in response to forces. Thus, if an implant is secured to this artery, its position relative to other intracranial structures will remain constant. This means that its registration relative to those structures is fixed more or less indefinitely. This confers significant advantages that are simply not available in other blood vessels.

Moreover, the middle meningeal artery also happens to be located at an ideal spot for interaction with the brain itself. It is inside the skull, which means that the skull will not absorb or scatter any energy. It is far away from any muscles, which are constantly emitting stray electric fields as they are being used.

This unique circumstance shields the implant from inadvertent motion that results from external manipulation. Such inadvertent motion is a significant risk when placing the implant in a blood vessel at some other location such as the scalp, the face, or the neck.

The implant thus enjoys an ideal perch from which to measure both linear and angular accelerations of the skull. The fact that the implant is securely nestled within the groove means that its reference frame and that of the skull are identical. This element of criticality does not exist when the implant is placed at another location.

Precise measurements of acceleration using micro-sensors such as gyroscopes, gyrometers, and accelerometers are of interest for providing a quantitative basis for establishing thresholds for traumatic brain injury. The use of an implant as described herein is far more accurate than placing similar instrumentation on a helmet because the acceleration of a helmet in response to an impact is not the same as the acceleration of the skull itself. In fact, the whole point of a helmet in the first place is to is to isolate the skull from the impact. Thus, the better the helmet works, the less suitable it becomes as a platform from which to measure acceleration of the skull itself.

In another aspect, the invention features a method that includes endovascularly passing an implant to the middle meningeal artery by being passed through blood vessels. The implant includes a carrier that carries a payload and an anchor mechanism that anchors the implant to the middle meningeal artery.

Some practices include passing the implant through the blood vessels while an anchor mechanism of the implant is gradually transitioning into a swollen state and reaching the middle meningeal artery before the swelling is complete.

Some practices further include leaving the implant in the middle meningeal artery so that it blocks flow of blood in that artery, thus depriving the surrounding brain tissue of at least some oxygenated blood that would otherwise have been delivered by the middle meningeal artery.

BRIEF DESCRIPTION OF THE DRAWINGS

These and other features of the invention will be apparent from the following detailed description and the accompanying figures, in which.

DETAILED DESCRIPTION

Figure 1:
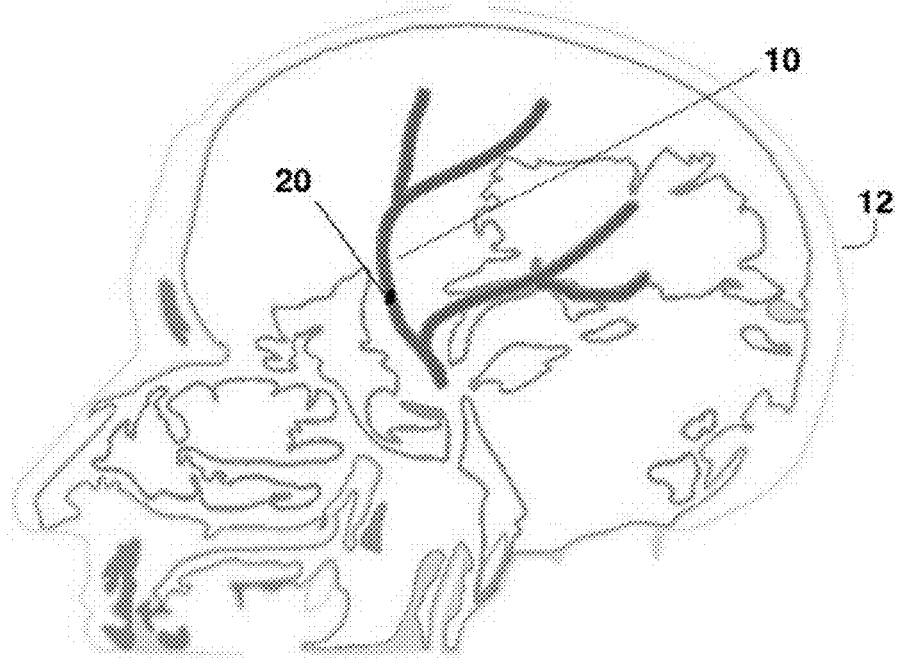
FIG. 1 shows the location of the middle meningeal-artery from the temporal aspect.

FIG. 1 shows a temporal view of the middle meningeal-artery 10. The middle meningeal-artery 10 has certain properties that lend itself to being used as a site of placement of an implant that can interact intimately with tissues contained within the skull 12.

First of all, the middle meningeal-artery 10 is easily accessed using standard widely available microcatheter-based techniques. One can easily reach it through endovascular surgical methods, such as through trans-femoral or trans-arterial insertion.

Secondly, the middle meningeal-artery 10 is not particularly essential. As shown in FIG. 1, it is part of an associated network that provides a considerable collateral blood supply. This means that it can be occluded or sacrificed without undue or irreversible damage or injury.

Figure 2:
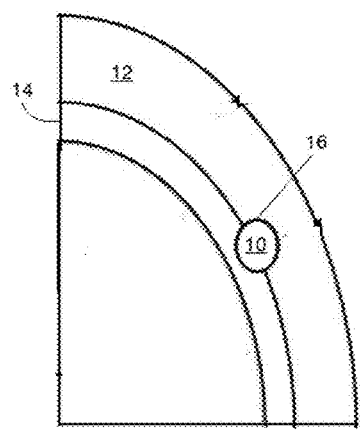
FIG. 2 is a cross-section showing the location of the middle meningeal-artery relative to the skull and the dura mater.

A third property of the middle meningeal-artery 10 is its location relative to the dura mater 14. This can be seen in FIG. 2, which shows the middle meningeal-artery 10 stabilized by being within a groove 16 in the inner surface of the skull 12 and also surrounded by the dura mater 14.

Accordingly, the middle meningeal-artery 10 is close to the brain's parenchyma. And it is also contained in a protective structure that is immovable relative to the skull 12. As such, it forms an exceptionally stable perch from which one can interact intimately with the parenchyma. This unique arrangement provides the middle meningeal-artery 10 with mechanical stability and considerable protection from external forces, including even moderate head trauma. Because of its close association with the dura mater 14, it is also exposed to intracranial pressure.

Figure 3:
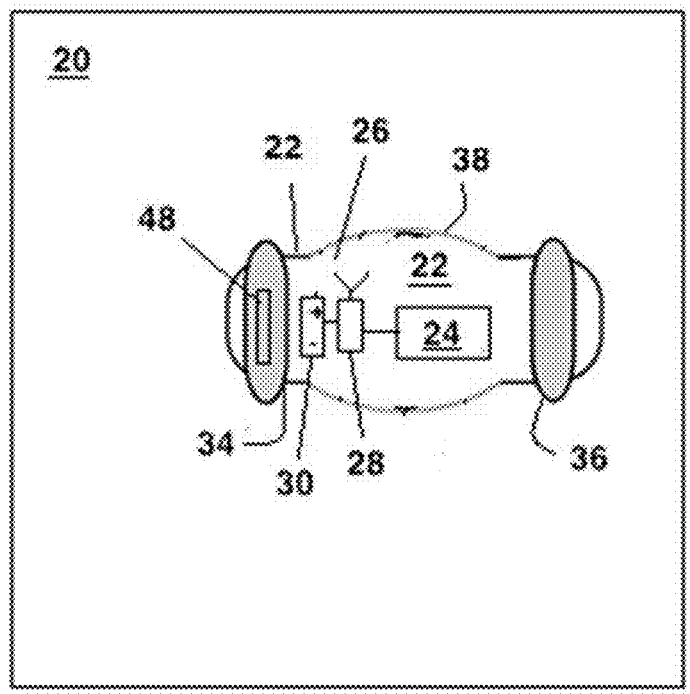
FIG. 3 shows an implant for implantation into the middle meningeal-artery shown in FIGS. 1 and 2.

Referring now to FIG. 3, an implant 20 to be deployed within the middle meningeal-artery 10 features a carrier 22 that carries different payloads 24 for carrying out different functions together with certain components that are agnostic to the type of payload 24. These components include an antenna 26 and circuitry 28 for carrying out any data analysis on data collected by the payload 24 and interfacing between the payload 24 and the antenna 26.

In some embodiments, a power supply 30 provides power for operating the circuitry 28 and the payload 24. In a typical implementation, the power supply 30 is a battery. However, other embodiments use power supplied by an interrogating source. Such embodiments omit the power supply 30.

Figure 4:
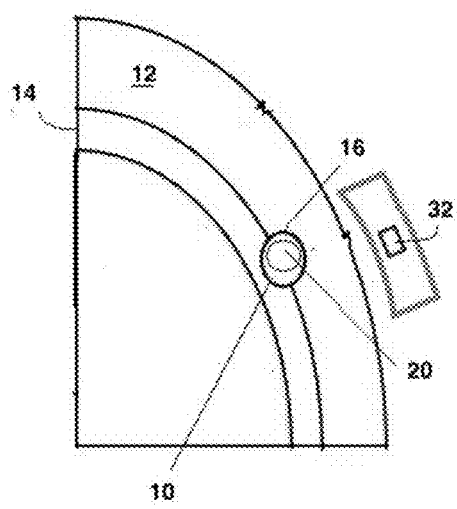
FIG. 4 shows a controller located outside the skull and in communication with the implant of FIG. 3.

In one implementation, the patient wears a helmet or a strap that holds a controller 32, as shown in FIG. 4. The controller 32 is thus close enough to communicate with the implant 20. Alternatively, a pair of glasses holds the controller 32. In some embodiments, the controller 32 is an app executing on a smart phone. Where privacy is of concern or where there exists a possibility of tampering, the circuitry 28 and the controller 32 both feature an encryption and decryption mechanism so that communication between the implant 20 and the controller 32 can be encrypted.

The implant 20 further includes an anchoring mechanism to anchor the implant 20 to the wall of the middle meningeal artery 10. In some embodiments, the anchoring mechanism includes an anchor that transitions between a deployment state and an anchoring state. With the anchor in the deployment state, the implant 20 moves freely through the vascular system. But once the anchor reaches the anchoring state, it can no longer be moved.

In some embodiments, the anchor transitions slowly into its anchoring state so that enough time is available to maneuver the implant 20 to the correct position before it can no longer be moved.

Among these are anchors that begin a transition into the anchoring state upon exposure to bodily fluids. Such anchors can be made by a material that slowly absorbs bodily fluids and becomes increasingly turgid and swollen as it does so until it is so swollen that it can no longer fit through a blood vessel. A suitable material with these properties is hydrogel.

The resulting delay in swelling defines a window of opportunity during which a surgeon can endovascularly insert the implant 20. This window is long enough to make it easy to catheterize the middle meningeal-artery 10 with an appropriately-sized microcatheter that has been delivered via a transfemoral or transarterial approach.

Once in the middle meningeal-artery 10, the surgeon uses the implant's delivery microwire to maneuver it into a suitable position to be detached. Detachment can be carried out electrolytically, mechanically, or hydraulically.

Anchors can be made in a variety of shapes. In some cases, anchors are discrete structures around the periphery and placed such that, as they swell, they contact each other to form an annulus. In other cases, the anchors are annular anchors to begin with. In other cases, the anchors are mechanical self-expanding spikes or anchors. In other cases, anchors can be membranes that are inflated by instillation or infusion of fluid.

FIG. 3 shows first and second toroidal anchors 34, 36 that flank a carrier 22 at opposite ends thereof. These toroidal anchors 34, 36, when swollen with bodily fluids, swell enough to completely fill the space between the carrier 22 and a wall of the blood vessel and to exert enough pressure to anchor the carrier 22 to the wall of the blood vessel.

Once in position, the first and second toroidal anchors 34, 36 gradually absorb bodily fluids and begin to swell. By this time, the carrier 22 should have been safely delivered to the middle meningeal-artery 10. The swelling causes the first and second toroidal anchors 34, 36 to anchor the carrier 22 within the middle meningeal-artery 10. In addition, the first and second toroidal anchors 34, 36 occlude blood flow through the middle meningeal-artery 10. Depending on the function of the payload 24, occlusion of blood flow offers certain advantages.

The swollen first and second toroidal anchors 34, 36 thus immobilize the carrier 22, thereby anchoring the carrier 22 to the artery's wall and preventing migration.

In some embodiments, the carrier 22 takes the form of a tubular body 38. In such embodiments, the first and second toroidal anchors 34, 36 and the tubular body 38 cooperate to isolate and seal a central portion of the tubular body 38, thus isolating it from blood and from variations in blood pressure.

Figure 5:
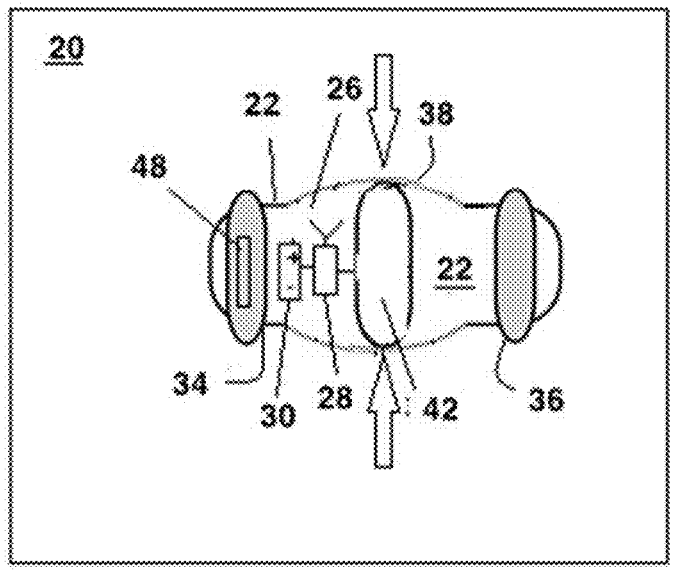
FIG. 5 shows the implant of FIG. 3 carrying a pressure sensor as its payload.

Referring now to FIG. 5, one example of a payload 24 is a pressure sensor 42. Such a payload 24 is particularly useful prior or to brain surgery and in the recovery period that follows. A pressure sensor 42 makes it possible to monitor intracranial pressure in patients with ventricular cerebrospinal fluid shunts or external ventricular drainage systems, both of which are prone to clogging.

Symptoms of clogging or other malfunctions of such devices can be difficult to discriminate from non-specific headache or constitutional symptoms. These result in frequent visits to emergency rooms or frequent hospitalization, accompanied by instrumentation of the valve assembly, such as placing a needle into the shunt valve or reservoir, and surgical exploratory/revision surgery. As such, it is useful to avoid false alarms.

A carrier 22 with a pressure sensor 42 would enable the patient or the caregiver to rapidly scan the data and obtain a history of the intra-cranial pressure, together with a real-time measurement. This will permit rapid and reliable identification of actual shunt malfunctions.

The wall of the tubular body 32 includes a membrane 40 at a central portion thereof. This membrane 40 contacts the wall of the middle meningeal-artery 10, which in turn contacts the dura mater. As a result, the membrane 40 is sensitive to intracranial pressure. The pressure sensor 42 is in mechanical communication with the membrane 40 can thus receive a signal indicative of intracranial pressure. Because the interior of the tubular body 32 is isolated from the blood, the ambient blood pressure cannot corrupt the resulting measurement.

Another application of the implant 20 as described in connection with FIG. 5 is in connection with non-invasive monitoring of patients with cerebral edema from traumatic brain injury. Such an implant 20 avoids the need for serial neurological examination or, in more advanced cases, placement of an invasive intracranial pressure monitor within the brain's parenchyma. This procedure requires breaching the skull with a burr hole, with the attendant risk of intracranial hemorrhage and infection, not to mention the obtrusive presence of instrumentation protruding from one's skill.

An implant 20 within the middle meningeal artery offers a simple minimally invasive endovascular procedure that avoids the need for systemic anticoagulation and that would be quick to perform. Once implanted, the implant 20 would enable constant intra-cranial pressure monitoring and shorten hospital days spent in intensive care as well as provide non-invasive measurements to help guide osmotic therapy and induced pharmacological sedation for intra-cranial pressure control.

Some embodiments of the implant 20 could be placed in the extradural space after a surgical procedure, such as after tumor surgery, to measure post-operative intra-cranial pressure and to monitor changes following intracranial hemorrhage evacuation surgery and or decompression for traumatic cerebral edema. The implant 20 could be attached to the inside surface of a cranial bone flap with a titanium mini-plate or screw. Alternatively, the implant 20 could be sutured to the dura during closing of a craniotomy.

Some embodiments include a variety of other sensors inside the tubular body 32. For example, in FIG. 6, the payload 24 includes an accelerometer 44 and a gyrometer 46 for measuring linear and angular acceleration.

Figure 6:
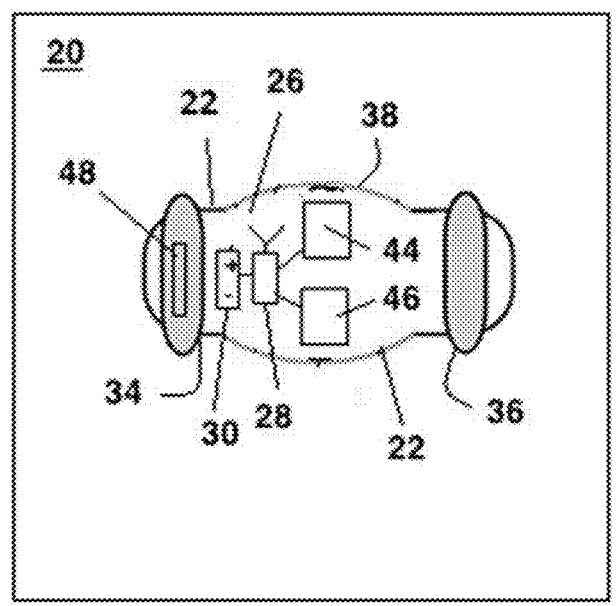
FIG. 6 shows the implant of FIG. 3 carrying a motion sensor as its payload.

Athletes and soldiers who are subjected to a high risk of repeated head injury or who may have incurred previous severe concussions and need careful longitudinal monitoring to insure rapid detection of cerebral edema would be suitable candidates for the elective placement of the implant 20 as shown in FIG. 6. A version of the implant 20 shown in FIG. 6 would permit acquisition of direct head-motion history, including events indicative of rapid acceleration. An implant 20 incorporating the accelerometer 44 and gyrometer 46 as shown in FIG. 6, when implanted as described shares the same inertial reference frame as the skull and would thus have significant advantages over a helmet or body-mounted device. Such an implant 20 would enable the exact quantification of target tissue events without the confounding factor of mismatches between acceleration of the helmet and that of the head as well as the need to infer acceleration of the head from acceleration of another part of the body, such as the torso, the abdomen, or the limbs. In addition, such an implant 20 could also transmit intracranial pressure information. Such information is useful for alerting a caregiver of the onset of brain swelling that would require treatment.

Figure 7:
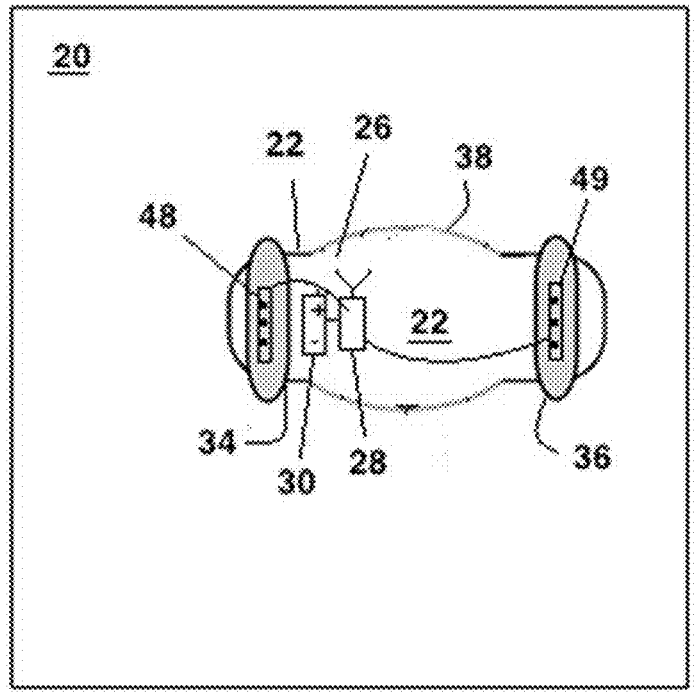
FIG. 7 shows implant of FIG. 3 carrying sets of electrodes as its payload.

In other embodiments, the payload 24 is integrated into the toroidal anchors 24, 26. For example, in the embodiment shown in FIG. 7 the payload 24 amounts to sets of electrodes 48, 49 embedded in the first and second toroidal anchors 24, 26 such that the electrodes 48 can make electrical contact with the wall of the artery. Such electrodes 48 can be used for collecting measurements of electrical signals, such as an EEG signals. Since the structure of the electrodes 48 is agnostic to the direction of energy flow, such electrodes 48 can also be used for electrical stimulation.

Figure 8:
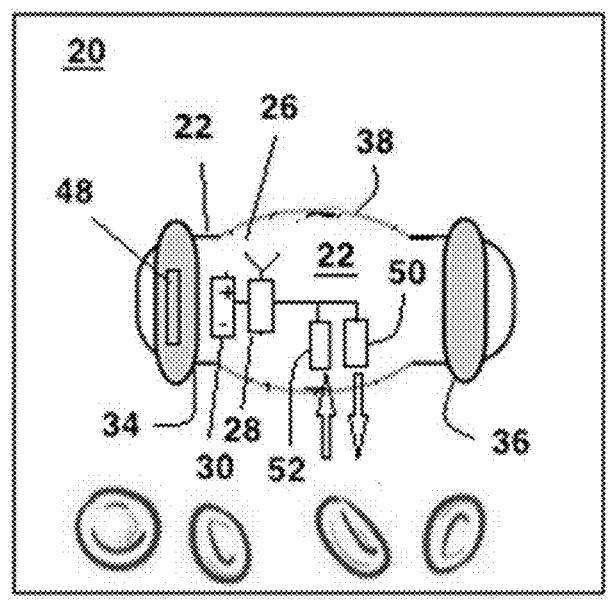
FIG. 8 shows the carrier of FIG. 3 carrying a pulse oximeter as its payload.

In another embodiment, shown in FIG. 8, the payload 24 includes one or more lasers 50 and a photodetector 52. For the case in which the laser 50 emits in the near infrared band, such a payload 24 is usable to carry out pulse oximetry and local brain tissue perfusion analysis.

Figure 9:
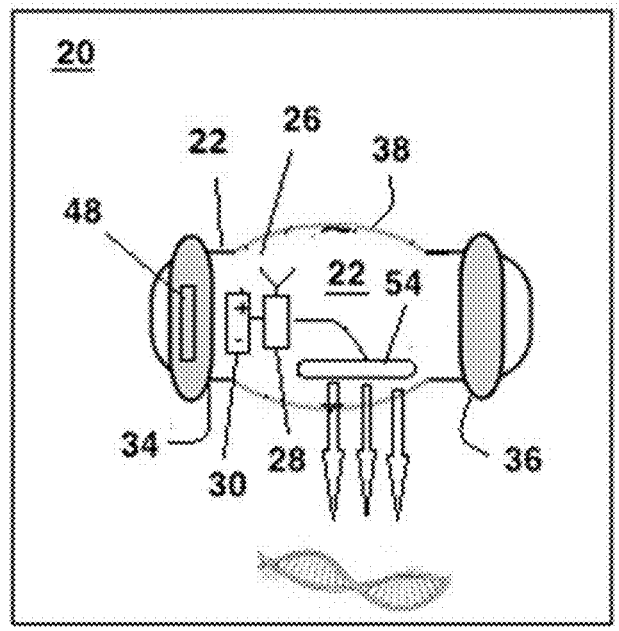
FIG. 9 shows the carrier of FIG. 3 carrying an optogenetic stimulator as its payload.

In another embodiment, shown in FIG. 9, the payload 24 includes a light-emitting array 54. Such a payload 24 is suitable for carrying out optogenetic stimulation. This provides a way to promote gene expression by illumination with light of a certain frequency and amplitude. In this embodiment, the circuitry 28 can be configured to control the light-emitting sources on the array 54 to illuminate a particular region with a desired amplitude, frequency and pattern of illumination so as to promote a desired pattern of gene expression in a certain pattern on the surface of the brain. The close proximity of the array 54 to the surface of the brain provides an advantageous way to provoke optogenetic response. An example of such optical activation is described in "A photoactivatable Cre-loxP recombination system for optogenetic genome engineering, Fuun Kawano, Risako Okazaki, Masayuki Yazawa & Moritoshi Sato, Nature Chemical Biology volume 12, pages 1059-1064 (2016))," the contents of which are herein incorporated by reference.

Figure 10:
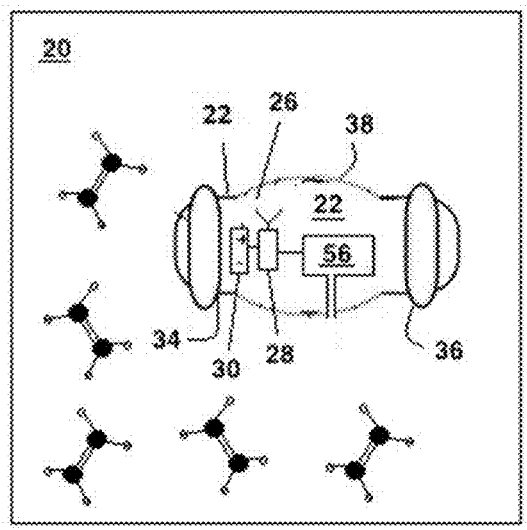
FIG. 10 shows the carrier of FIG. 3 carrying chemical sensor as its payload.

In another embodiment, shown in FIG. 10, the implant 20 includes a chemical sensor 56.

Figure 11:
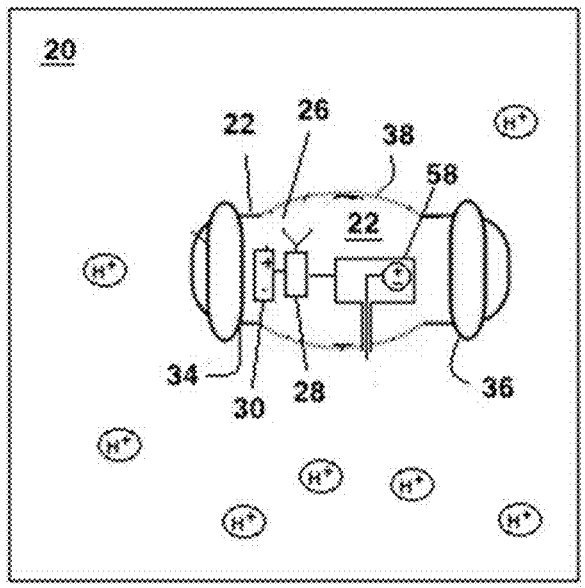
FIG. 11 shows the carrier of FIG. 3 carrying a pH sensor as its payload.

In another embodiment, shown in FIG. 11, the implant 20 includes a pH sensor 58.

Figure 12:
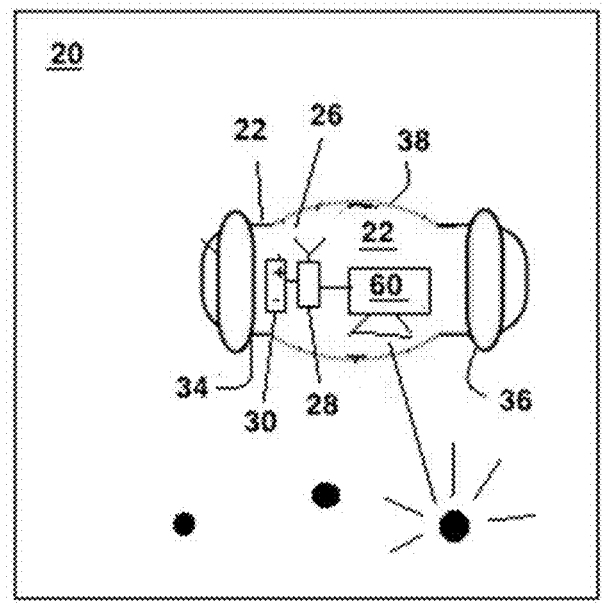
FIG. 12 shows the carrier of FIG. 3 carrying a fluorescence sensor as its payload.

In another embodiment, shown in FIG. 12, the implant 20 includes a fluorescence sensor 60.

Figure 13:
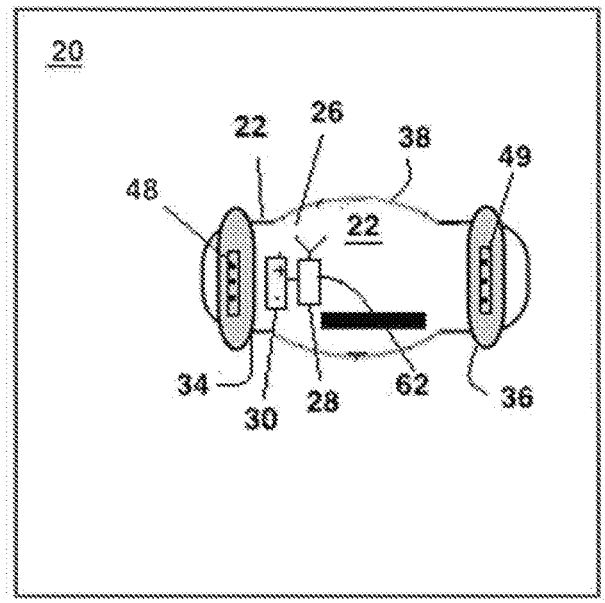
FIG. 13 shows the carrier of FIG. 3 carrying a biomarker chip as its payload.

In another embodiment, shown in FIG. 13, the implant 20 includes a biomarker chip 62.

Figure 14:
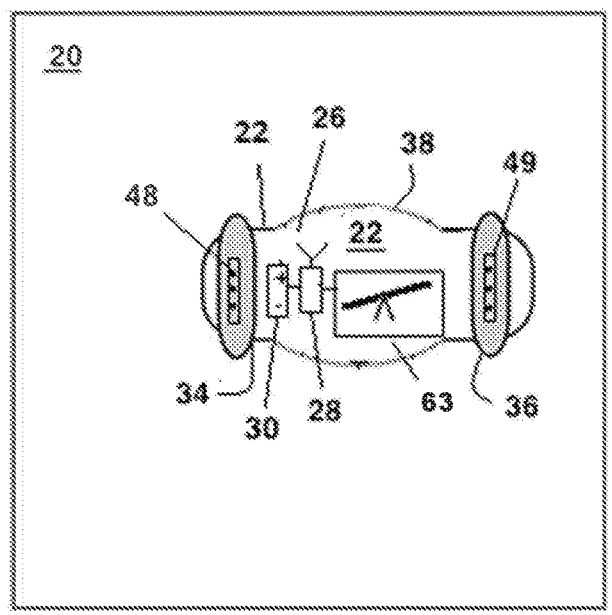
FIG. 14 shows the carrier of FIG. 3 carrying an orientation detector as its payload.

In another embodiment, shown in FIG. 14, the implant 20 includes an orientation detector 63, such as a level, that provides a measurement of orientation of the implant 20.

There is no requirement that an implant 20 carry only one of the foregoing payloads. An implant 20 can carry multiple combinations of any of the foregoing sensors.

Other types of implants 20 with different kinds of carriers 22 can be implanted into the middle meningeal-artery 10 in a similar manner.

Figure 15:
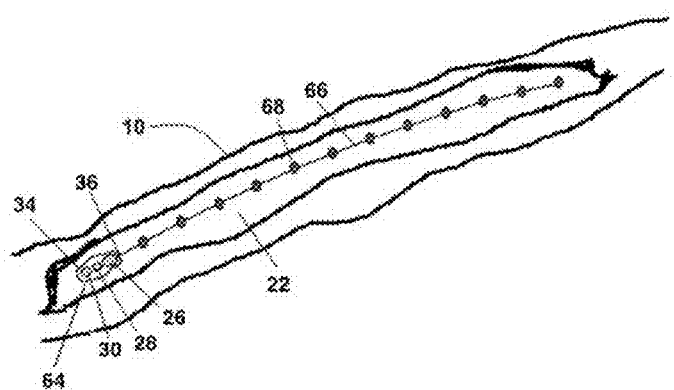
FIG. 15 shows an array of nodes anchored to the middle-meningeal artery.

For example, in an embodiment shown in FIG. 15, the carrier 22 is a loose wire 66 and the payload 24 takes the form of nodes 68 disposed thereon at regular intervals. The anchor 64 is formed by the first and second toroidal anchors 34, 36 that flank a body containing the antenna 26, power supply 30, and electronics 28. The anchor 64 couples to the wire 66 and thus anchors the array of nodes 68 to the middle meningeal-artery 10. This places it in a secure position at a place that is very close to the parenchyma. As a result, it is possible to electrically interact with the parenchyma with much higher signal-to-noise ratio.

In some embodiments, the nodes 68 are sensory electrodes function as a neural implant that can be used to either record signals emanating from the brain or to apply signals to carry out brain stimulation. Because of the placement of the implant, such stimulation includes surface stimulation. However, nothing precludes the implant from being used to carry out stimulation in intermediate layers of the brain proximate to the implant or even to carry out deep brain stimulation by, for example, use of phased-array stimulation techniques.

Signals received by the nodes 68 carry information concerning the state of the brain. When provided to suitable computational circuitry, such signals can form the basis of determining the existence of certain moods in the patient or the existence of certain neurological disorders. For example, certain patterns of spatial and temporal variation of signals can be correlated with mood disorders, such as depression.

Conversely, the nodes 68 can be used to apply voltages, thereby stimulating regions of the brain in a controlled manner. This creates the possibility of treatment of neurological disorders, such as depression, epilepsy, paralysis, and the like, by discovering or inferring patterns of stimulation that have neuro-therapeutic value.

In yet other embodiments, the nodes 68 are chemical sensors. Yet other embodiments include a combination of both of the foregoing.

Associated circuitry 28 provides control over the nodes 68. In addition, the associated circuitry 28 handles communication via an antenna 26 to the controller 32 as described in connection with FIGS. 3 and 4.

Figure 16:
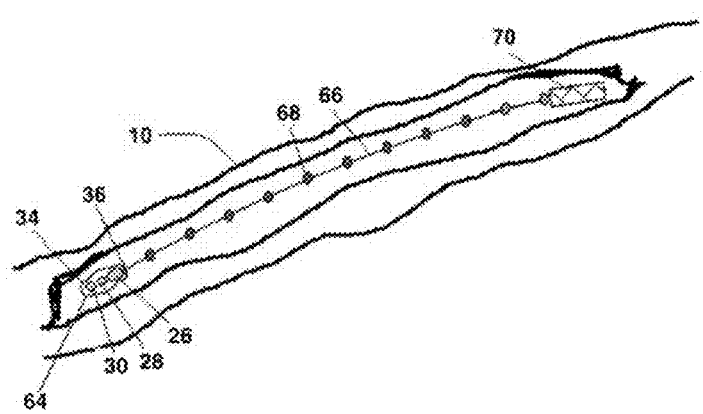
FIG. 16 shows an array of nodes anchored to two locations in the middle-meningeal artery

FIG. 16 shows an embodiment similar to that shown in FIG. 15 but with first a first anchor 64 at a first end of the wire 66 and a second anchor 70 at a second end of the wire 66. As a result, both ends of the wire 66 are anchored.

Having described the invention, and a preferred embodiment thereof, what we claim as new and secured by Letters Patent is:

1. An apparatus comprising an implant for endovascular delivery via a catheter to a middle-meningeal for implantation therein, said catheter being withdrawn following implantation of said implant, said implant comprising a carrier, an anchor mechanism, and a payload, wherein said payload is oriented to engage in energy transfer with brain tissue in a direction towards a wall of said middle meningeal artery, wherein said implant is sized and shaped to be endovascularly delivered to the middle meningeal artery, wherein said anchor mechanism is configured to anchor said implant to said middle meningeal artery, and wherein said carrier carries said payload.

2. The apparatus of claim 1, wherein said implant is a first implant, wherein said payload is a first payload, wherein said apparatus further comprises a second implant having a carrier that carries a second payload and an anchor mechanism for anchoring said second implant within said middle meningeal artery, wherein said first payload controls operation of said second payload.

3. The apparatus of claim 2, wherein said first and second implants carry different types of payload.

4. The apparatus of claim 1, wherein said anchor mechanism is configured to transition into a swollen state, wherein, in said swollen state, said anchor mechanism anchors said implant to said middle meningeal artery, and wherein, prior to completing said transition, said anchor mechanism permits endovascular delivery of said implant to said middle meningeal artery.

5. The apparatus of claim 1, wherein said anchor mechanism comprises a first anchor and a second anchor, wherein said first anchor is disposed on one side of said payload and at a first end of said carrier, and wherein said second anchor is disposed on another side of said payload and at a second end of said carrier.

6. The apparatus of claim 1, wherein said anchor mechanism comprises a toroidal anchor disposed around said implant, wherein said toroidal anchor swells in response to exposure to bodily fluids.

7. The apparatus of claim 1, wherein said anchor mechanism comprises a hydrogel layer that surrounds said implant.

8. The apparatus of claim 1, wherein said anchor mechanism comprises first and second toroidal anchors axially displaced from each other, wherein, in response to exposure to bodily fluids, said first and second toroidal anchors transition between a first size that permits delivery of said implant to said middle meningeal artery and a second size that is too large to pass through said middle meningeal artery.

9. The apparatus of claim 1, further comprising a second implant, wherein said second implant is configured to receive, from said first implant a signal having traversed an expanse of brain tissue between said first implant and said second implant.

10. The apparatus of claim 1, wherein said anchor mechanism forms an occlusion configured to occlude said middle meningeal artery, wherein said anchor mechanism begins to form said occlusion during delivery of said implant to said middle meningeal artery and completes formation of said occlusion after said implant has been delivered to said middle meningeal artery.

11. The apparatus of claim 1, wherein said anchor mechanism comprises an annular anchor that spontaneously transitions from a first state into a second state, wherein, in said first state, said annular anchor has an outer diameter that is smaller than an inner diameter of said middle meningeal artery, and wherein, in said second state, said annular anchor would have an outer diameter larger than an inner diameter of said middle meningeal artery if said annular anchor were outside of said middle meningeal artery.

12. The apparatus of claim 1, wherein said carrier comprises a tubular body and wherein said payload is disposed inside the tubular body.

13. The apparatus of claim 1, wherein said carrier comprises a flexible wire and said payload is disposed on said flexible wire.

14. The apparatus of claim 1, wherein said carrier comprises a flexible wire and said anchor mechanism comprises anchors at either end of said flexible wire.

15. The apparatus of claim 1, wherein said implant comprises an antenna and a communication system for communication with a controller outside a patient into which said implant has been implanted.

16. The apparatus of claim 1, wherein said carrier comprises a flexible wire and said payload comprises nodes along said wire, each of said nodes being selected from the group consisting of a sensor and a stimulator, and wherein said anchoring system comprises first and second stents that engage opposite ends of said wire.

17. The apparatus of claim 1, wherein said anchor mechanism is configured to sustain an increase in mass after having entered a patient.

18. The apparatus of claim 1, further comprising a neural implant, wherein said implant is a constituent neural interface of said neural implant for use in one of brain stimulation and recording signals from the brain.

19. The apparatus of claim 1, wherein said carrier comprises a flexible wire and said payload comprises a plurality of electrodes disposed on said flexible wire.

20. The apparatus of claim 1, wherein said payload comprises a communication system that receives a signal from a collateral implant and uses said signal as a basis for feedback control of said collateral implant.

21. The apparatus of claim 1, wherein said payload is configured for executing feedback control of a pacemaker.

22. The apparatus of claim 1, wherein said payload comprises one of a light-emitting source and a light-sensing receiver.

23. The apparatus of claim 1, wherein said payload comprises one of a source of acoustic energy and a sensor for receiving acoustic energy.

24. The apparatus of claim 1, wherein said payload comprises a biomarker chip.

25. The apparatus of claim 1, wherein said payload is configured to measure temperature.

26. The apparatus of claim 1, wherein said payload is configured to measure hydrogen ion concentration.

27. The apparatus of claim 1, wherein said payload is configured to detect motion.

28. The apparatus of claim 1, wherein said payload comprises a membrane configured to contact a wall of said artery that faces dura matter and a pressure sensor in contact with said wall for measuring intra-cranial pressure.

29. The apparatus of claim 1, wherein said carrier comprises a flexible wire and said payload comprises nodes along said wire, each of said nodes being selected from the group consisting of a sensor and a stimulator.

30. A method comprising endovascularly delivering an implant to the middle meningeal artery, said implant comprising a carrier that carries a payload and an anchor mechanism that anchors said implant to the middle meningeal artery, wherein said payload is oriented to engage in energy transfer with brain tissue in a direction towards a wall of said middle meningeal artery, and wherein endovascularly delivering comprises using a catheter to deliver said implant and removing said catheter after said implant has been delivered.

* * * * *